US012618058B2

(12) United States Patent
Hoelke et al.

(10) Patent No.: US 12,618,058 B2
(45) Date of Patent: *May 5, 2026

(54) BLENDS CONTAINING PROTEASES

(71) Applicant: Roche Diagnostics Operations, Inc., Indianapolis, IN (US)

(72) Inventors: Werner Hoelke, Penzberg (DE); Michaela Fischer, Geretsried (DE); Johann-Peter Thalhofer, Weilheim (DE); Markus Weber, Habach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 457 days.

This patent is subject to a terminal disclaimer.

(21) Appl. No.: 17/822,587

(22) Filed: Aug. 26, 2022

(65) Prior Publication Data

US 2023/0052545 A1     Feb. 16, 2023

Related U.S. Application Data

(63) Continuation of application No. 16/865,487, filed on May 4, 2020, now Pat. No. 11,459,556, which is a continuation of application No. 15/595,126, filed on May 15, 2017, now abandoned, which is a continuation of application No. 14/699,299, filed on Apr. 29, 2015, now abandoned, which is a continuation of application No. 13/230,927, filed on Sep. 13, 2011, now abandoned, which is a continuation of application No. PCT/EP2010/001687, filed on Mar. 17, 2010.

(30) Foreign Application Priority Data

Mar. 19, 2009   (EP) ..................................... 09003967
Apr. 9, 2009    (EP) ..................................... 09005257

(51) Int. Cl.
  *C12N 9/50*      (2006.01)
  *C12N 9/52*      (2006.01)
  *C12N 9/54*      (2006.01)
  *C12N 9/64*      (2006.01)
  *C12N 9/96*      (2006.01)

(52) U.S. Cl.
  CPC ............. *C12N 9/6489* (2013.01); *C12N 9/52* (2013.01); *C12N 9/54* (2013.01); *C12N 9/6491* (2013.01); *C12N 9/96* (2013.01); *C12Y 304/24003* (2013.01); *C12Y 304/24027* (2013.01)

(58) Field of Classification Search
  CPC ....... C12N 9/6491; C12N 9/6489; C12N 9/96
  See application file for complete search history.

(56) References Cited

U.S. PATENT DOCUMENTS 5,739,023 A     4/1998   Harada et al.

FOREIGN PATENT DOCUMENTS

| CA | 2469137 A1 | 1/2005 |
|---|---|---|
| EP | 1496112 A2 | 1/2005 |
| EP | 2161333 A1 | 3/2010 |
| WO | 1998024889 A1 | 6/1998 |
| WO | 2002048318 A1 | 6/2002 |

OTHER PUBLICATIONS

Liberase MNP-S GMP Grade. Roche. Retrieved on Apr. 7, 2025.*
Bucher et al., Optimization of Neutral Protease to Collagenase Activity Ration for islet of Lengerhans Isolation, Transplantation Proceedings, 2004, vol. 36, pp. 1145-1146.
Endo, S., Studies on Protease Produced by Themphilic Bacteria, Journal of Fermentation Technology, 1962, pp. 346-353, vol. 40, No. 1.
Fach et al., Neonatal Ovine Pulmonary Dendritic Cells Support Bovine Respiratory Syncylial Virus Replication with Enhanced interleukin (IL) and IL-10 Gene Transcripts; Viral Immunol., 2007, vol. 20, No. 1, pp. 119-130.
Feder et al., Studies on the Role of Calcium in Thermolysin; Biochemistry, 1971, vol. 10, No. 24, pp. 4552-4556.
Inouye et al., Effect of amino acid residues at the cleavable site of substrates ont eh remarkable activation of thermolysin by salts, Biochemistry Journal, 1996, vol. 315, pp. 133-138.
Inouye et al., Effect of Salts on the Solubility of Thermolysin: A Remarkable Increase in the Solubility as Well as the Activity by the Addition of Salts without Aggregation or Dispersion of Thermolysin, Journal of Biochemistry, 1998, pp. 847-852, vol. 123.
Att, el al., Thermolysin: A Zinc Melalloenzyme, Biochemical and Biophysical Research Communications, 1969, vol. 37, No. 2, pp. 333-339.
Matsubara, et al., Other Bacterial, Mold, and Yeast Proteases, The Enzymes, 1971, 3rd Edition, vol. 3, Ch. 20, pp. 1721-1755.
Morihara, Kazuyuki and Tsuzuki, Hiroshige, Thermolysin: Kinetic Study with Oligopeptides, European Journal of Biochemistry, 1970, vol. 15, pp. 374-380.
Noyes, Arthur A. and Whitney, Willis R., The Rate of Solution of Solid Substances in Their Own Solutions, Journal of the American Chemical Society, 1897, vol. 19, No. 12, pp. 930-934.
O'Donohue et al., Cloning and expression in Bacillus subtilis of the npr gene from Bacillus themoproteolyticus Rokko coding for thermostable metalloprotease thermolysin; Biochemistry Journal, 2003, vol. 300, pp. 399-603.
Roche, Inc., Liberase MNP-S GMP Grade, Product Information Sheet, 1996, 1 page.
Sigma-Aldrich, RPMI-1640 Media Formulation, Product Information Sheet, 2014, 5 pps.

(Continued)

*Primary Examiner* — Yong D Pak
(74) *Attorney, Agent, or Firm* — Taft Stettinius & Hollister LLP

(57) ABSTRACT

Described are compositions, in particular lyophilizates, containing proteolytic enzymes, and methods for producing the compositions. Typically these compositions contain one or more proteases with collagenase activity and a neutral protease, for example, thermolysin. The compositions are free of acetate salts. Surprisingly, such compositions can be dissolved in water more rapidly than lyophilized protease mixtures of the state of the art.

16 Claims, 2 Drawing Sheets

(56)         References Cited

OTHER PUBLICATIONS

Tajima, Masahiro et al., Role of Calcium Ions in the Thermostability of Thermolysin and *Bacillus subtilis* var. amylosacchariticus Neutral Protease, European Journal of Biochemistry, 1976, vol. 64, pp. 243-247.
International Search Report, European Patent Office, International Patent Application No. PCT/EP2010/001687, Jun. 25, 2010, 4 pages.
Written Opinion of the International Searching Authority, European Patent Office, International Patent Application No. PCT/EP2010/001687, Jun. 25, 2010, 9 pages.
International Preliminary Report on Patentability, European Patent Office, International Patent Application No. PCT/EP2010/001687, Sep. 20, 2011, 10 pages.

\* cited by examiner

BLENDS CONTAINING PROTEASES

RELATED APPLICATIONS

This application is a continuation application of U.S. application Ser. No. 16/865,487 filed May 4, 2020, which is a continuation of U.S. application Ser. No. 15/595,126 filed May 15, 2017 (abandoned), which is a continuation of U.S. application Ser. No. 14/699,299 filed Apr. 29, 2015 (abandoned), which is a continuation of U.S. application Ser. No. 13/230,927 filed Sep. 13, 2011 (abandoned), which is a continuation of PCT/EP2010/001687 filed Mar. 17, 2010, and claims priority to European Application Nos. EP 09005257.2 filed Apr. 9, 2009 and EP 09003967.8 filed Mar. 19, 2009, the disclosures of which are hereby incorporated by reference in their entity.

FIELD

The present invention provides compositions, preferably lyophilizates, comprising proteolytic enzymes. Preferred compositions comprise one or more proteases with collagenase activity and a neutral protease, preferably thermolysin. According to the invention, the compositions are free of acetate salts. Surprisingly, such compositions can be dissolved in water more rapidly than lyophilized protease mixtures of the state of the art.

BACKGROUND

The process of disintegrating a mass of interconnected cells (tissue) wherein the cells are separated from each other is known as "tissue dissociation". Tissue dissociation is a principal application for certain proteolytic enzymes in tissue culture research and cell biology studies. Blends of proteolytic enzymes, rather than single proteases, are used for the dissociation of biological tissue.

The biological tissue is preferably obtained (i.e., explanted) from an animal, preferably from a mammal, and more preferred from a human. The biological tissue is incubated in an aqueous medium containing the proteolytic enzymes in active form. By way of hydrolyzing peptidic bonds in the extracellular matrix, the interconnected cells become separable from each other.

Despite the widespread use of enzymes for these applications over the years, many parameters influencing the tissue dissociation process and the harvesting of dissociated target cells are not well understood. As a result, the skilled person's choice of one particular protease or blend of proteases, or one certain technique over another has often been arbitrary and based more on past experience than on an understanding of why the protease-mediated process works and what modifications could lead to even better results.

Due to the fact that collagen has a major structural role in the preferred tissues, proteolytic enzymes with collagenase activity are used with advantage in many processes of tissue dissociation known to the art. Blends containing a plurality of proteases usually comprise collagenases.

Collagenases (EC 3.4.24.3) are metalloproteinases, proteolytic enzymes which are able to hydrolyze collagen, both in its native triple-helix and denatured conformation, by dissociating its peptidic bonds under physiological conditions of pH and temperature. Several collagenases produced by bacteria are well known in the state of the art. Collagenases produced by bacteria of the *Clostridium* species, in particular *Clostridium* hystolyticum are of major interest for applications in tissue dissociation.

In aqueous solution, the collagenases and particularly collagenase I are stable only to a limited extent, even at low temperatures. Particular care is in fact necessary when preparing and handling collagenase solutions, in order to prevent inactivation of enzymatic activity: a temperature above 56° C. is detrimental, as well as the presence of several metal ions and of chelating agents interacting with the Ca2+ ions that are essential in the collagenase structure. The optimal pH value for the storage of collagenases ranges from about 6 to about 8 for crude preparations, while the interval is much narrower when the collagenase isoforms are purified; low pH values can inactivate enzymatic activity. Besides, collagenases are sensitive to physical treatment such as freezing, thawing, lyophilization and drying. These treatments, which are often necessary for the purification and preparation of dry products, pose a technical problem in that they may reduce the desired enzymatic activity or may even provoke inactivation of the collagenase enzymes. Collagenase I and/or II isoforms in their lyophilized powder form maintain reasonable stability if kept at temperatures which are lower than 25° C., preferably between about 2° C. and 8° C., in sealed bottles and avoiding exposure to humidity. However, the low stability of collagenase isoforms in the presence of water and particularly in the added presence of a further protease such as thermolysin or dispase determines several problems in the preparation of blends, lyophilizates, and compositions for use in tissue dissociation.

Thermolysin [EC 3.4.24.27; CAS registry number 9073-78-3] is a thermostable neutral metalloproteinase (also referred to herein as "neutral protease") produced in the culture broth of *Bacillus thermoproteolyticus* (Endo, S., J., Ferment. Technol. 40 (1962) 346-353; Matsubara, H., Feder, J., in: 3rd ed., Boyer, P., D., (Ed.), The Enzymes, Vol. 3, Academic Press, New York, 1971, pp. 721-795). It requires one zinc ion for enzyme activity and four calcium ions for structural stability (Latt, S., A., et al., Biochem. Biophys. Res. Commun. 37 (1969) 333-339; Feder, J., et al., Biochemistry 10 (1971) 4552-4556; Tajima, M., et al., Eur. J. Biochem. 64 (1976) 243-247) and catalyzes specifically the hydrolysis of peptide bonds containing hydrophobic amino acid residues (Morihara, K., and Tsuzuki, H., Eur. J. Biochem. 15 (1970) 374-380; Inouye, K., et al., Biochem. J. 315 (1996) 133-138).

Roche Applied Science has developed LIBERASE enzymes (commercially available from Roche Diagnostics GmbH, Mannheim, Germany) which are blends of highly purified enzymes, designed to improve the quality and reproducibility of tissue dissociation, and improve the health of isolated cells. LIBERASE enzyme technology comprises the methods for purifying Clostridial collagenase isoforms to high specific activity, and for blending them together with high specific activity neutral protease in optimal ratios for effective dissociation of primary tissues. In the manufacturing process highly purified collagenase I and collagenase II are collected. These two collagenase isoforms are blended in a predetermined ratio with each other, and with a non-Clostridial neutral protease. The type of neutral protease is specifically chosen, and differs according to the final product. For example, LIBERASE Blendzyme 1 contains the neutral protease dispase, and LIBERASE Blendzyme 2 contains the neutral protease thermolysin.

LIBERASE enzymes are available for customers as lyophilizates; the same applies to a number of products from other manufacturers (e.g., Worthington Biochemical Corporation, Lakewood, N.J., USA) for the same intended use. The lyophilizates known to the art comprise one or more collagenase enzyme and/or one or more further protease, such as (but not limited to) thermolysin and dispase. In addition, the lyophilizates comprise certain helper substances which are present in the enzyme preparation or enzyme mixture, and which stabilize one or more enzymes in solution and/or during lyophilization. In addition, certain proteolytic enzymes can be crystallized in the presence of a helper substance. The solid material obtained upon crystallization can therefore also contain the helper substance.

Freeze-drying, also referred to as lyophilization or cryo-desiccation, is a dehydration process typically used to preserve a perishable material or make the material more convenient for storage and/or transport. Freeze-drying works by freezing the material and then reducing the surrounding pressure and adding enough heat to allow the frozen water in the material to sublime directly from the solid phase to gas.

Before use, any lyophilisate comprising one or more proteases has to be dissolved. The inventors have surprisingly found that one can dramatically reduce the time needed to dissolve a lyophilisate comprising a blend of collagenase enzymes and a neutral protease. The key to an enhanced solubility appears to be certain ionic compounds. In the presence of these compounds lyophilized protease material gains an improved contact with the aqueous solvent which aids dissolving the proteases. The time between contacting the lyophilisate with the aqueous solvent and complete solubilization of the lyophilizate is a crucial parameter limiting the quality of the proteolytic agents. The shorter this period, the less the proteolytic enzymes degrade each other, the more proteolytic activity is applied to the target tissue to be dissociated. Apart from shortening the absolute time span needed for solubilizing the lyophilizate, the variation of said time span could be minimized, too. This is particularly advantageous in terms of reproducibility of the enzymatic activity applicable in the subsequent tissue dissociation workflow. The smaller the variation, the higher the reproducibility.

SUMMARY

A first embodiment of the invention is a solid composition obtainable by the steps of (a) preparing a homogeneous solution of an acetate-free preparation of a neutral protease in an aqueous acetate-free low-salt solution; (b) adding a neutral salt to the homogeneous solution of step (a) and dissolving the neutral salt, thereby making a stabilized solution wherein said stabilized solution additionally comprises a buffer salt buffering in the range of about pH 6 to about pH 8.5, and wherein the stabilized solution further comprises calcium chloride; (c) mixing the stabilized solution of step (b) with an acetate-free preparation of one or more proteolytic enzymes with collagenase activity, and making a homogeneous solution; (d) freeze-drying the solution of step (c), thereby obtaining the solid composition of the invention.

A further embodiment of the invention is a solid composition obtainable by the steps of (a) dissolving an acetate-free preparation of a neutral protease, preferably thermolysin from *Bacillus thermoproteolyticus*, in an aqueous acetate-free low-salt solution, wherein the solution comprises a buffer salt capable of buffering in the range of about pH 6 to about pH 8.5 and further comprises calcium chloride, and making a homogeneous solution; (b) adding a neutral salt to the homogeneous solution of step (a) and dissolving the neutral salt, thereby making a stabilized solution; (c) mixing the stabilized solution of step (b) with an acetate-free preparation of one or more proteolytic enzymes with collagenase activity, and making a homogeneous solution; (d) freeze-drying the solution of step (c); thereby obtaining the solid composition of the invention.

A further embodiment of the invention is a method to produce a composition according to the invention, the method comprising the steps of (a) dissolving an acetate-free preparation of a neutral protease, preferably thermolysin from *Bacillus thermoproteolyticus*, in an aqueous acetate-free low-salt solution, wherein the solution comprises a buffer salt capable of buffering in the range of about pH 6 to about pH 8.5 and further comprises calcium chloride, and making a homogeneous solution; (b) adding a neutral salt to the homogeneous solution of step (a) and dissolving the neutral salt, thereby making a stabilized solution; (c) mixing the stabilized solution of step (b) with an acetate-free preparation of one or more proteolytic enzymes with collagenase activity, and making a homogeneous solution; (d) freeze-drying the solution of step (c); thereby producing the solid composition of the invention.

Another embodiment of the invention is a solid composition comprising one or more proteolytic enzymes with collagenase activity and a neutral protease characterized in that the composition is free of acetate salt.

Yet, a further embodiment of the invention is a method to prepare a solution with proteases, comprising the step of contacting a composition according to the invention with water.

Yet, a further embodiment of the invention is an aqueous solution comprising water and a composition according to the invention.

Yet, a further embodiment of the invention is the use of an aqueous solution according to the invention for treating a biological tissue.

Yet, a further embodiment of the invention is a kit comprising one or more containers containing a composition according to the invention.

DETAILED DESCRIPTION

Figure 1A:
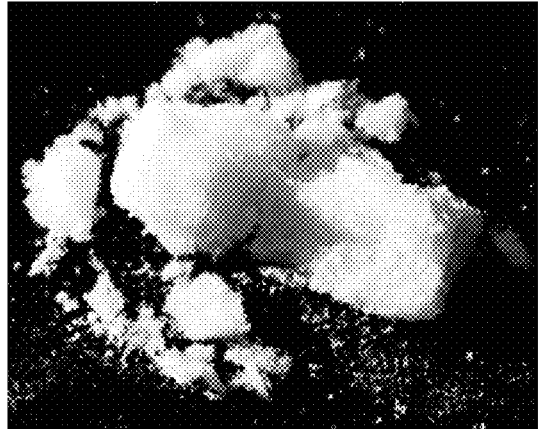
FIG. 1A shows a photograph of a lyophilizate with unordered clusters of crystals.

It was a surprising finding by the inventors that the surface area of a lyophilizate was greatly increased when the lyophilizate was prepared free of acetate salts. Typically, the lyophilizate according to the invention has a lamellar structure with an increased surface, compared to the lyophilizates known to the state of the art. Thus, the lyophilizates according to the invention have enhanced characteristics as to the time needed to dissolve them. This property is of great advantage because the time during which the proteases in solution degrade each other is significantly reduced.

In addition, the lyophilizates according to the invention are dissolved to form clear, homogeneous solutions. That is to say, no precipitate occurs. Thereby protease solutions of high, reproducible quality are provided.

Certain technical terms are used with particular meaning, or are defined for the first time, in this description of the present invention. For the purposes of the present invention, the terms used are defined by their art-accepted definitions, when such exist, except that when those definitions conflict or partially conflict with the definitions set forth below. In the event of a conflict in definition, the meaning of a term is first defined by any of the definitions set forth below.

The term "comprising" is used in the description of the invention and in the claims to mean "including, but not necessarily limited to".

The articles "a" and "an" are used herein to refer to one or to more than one (i.e., to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value which is equal to or lower than the second value. Thus, a value x in the designated range is given by $n1 \leq x \leq n2$.

If not stated otherwise, it is understood that the term "about" and the character "~" in combination with a numerical value n ("about n", "~n") indicates a value x in the interval given by the numerical value±5% of the value, i.e., $n-0.05*n \leq n \leq 0.05*n$. In case the term "about" or the character "~" in combination with a numerical value n describes a preferred embodiment of the invention, the value of n is most preferred, if not indicated otherwise.

A "mixture" is a substance made by combining two or more different materials with no chemical reaction occurring. The objects do not bond together in a mixture. A mixture can usually be separated back into its original components. Mixtures are the product of a mechanical blending or mixing of chemical substances like elements and compounds, without chemical bonding or other chemical change, so that each ingredient substance retains its own chemical properties and makeup. While there are no chemical changes in a mixture, physical properties of a mixture, such as its melting point, may differ from those of its components.

A lyophilizate is an example for a mixture which is a solid. In the context of the present invention such a mixture comprises one or more proteinaceous compounds. Preferably, these are one or more proteolytic enzymes with collagenase activity and a neutral protease. Preferably, the neutral protease is thermolysin. Also preferred, a lyophilizate additionally comprises a buffer salt, and further helper compounds which stabilize the proteinaceous compounds. The helper compounds can be ionic or non-ionic. Examples for ionic compounds are an organic salt and an inorganic salt. Examples for non-ionic compounds are an organic polymer (such as, but not limited to polyethylene glycol, and starch) and a polyol (such as, but not limited to a sugar and a sugar alcohol). Further helper compounds are possible.

Mixtures are either heterogeneous or homogeneous. Homogeneous mixtures are mixtures that have definite, consistent properties. Particles are uniformly spread. For example, any amount of a given mixture has the same composition and properties. A homogeneous mixture is a uniform mixture consisting of only one phase.

A solution is a homogeneous mixture of one or more substances (the solutes) dissolved (i.e., dissociated) in another substance (the solvent). A common example would be a solid dissolving into a liquid (i.e., salt or protein dissolving in water). Solubility is a compound property. Depending on the composition of the mixture to be dissolved and conditions (e.g., temperature, type of solvent, solutes present in the solvent), the amount of a substance that can dissolve in a solution can be variable.

Examples for non-homogeneous (heterogeneous) mixtures are a colloid and a suspension. In the context of the invention, a suspension is understood as being a heterogeneous fluid containing solid particles that are sufficiently large for sedimentation. Unlike colloids, the suspended particles settle over time if left undisturbed. This distinguishes a suspension from a colloid in which the suspended particles are smaller and do not settle.

In a solution, the dissolved substance does not exist as a solid, and solute(s) and solvent are homogeneously mixed. The term "stability" of a solution refers to the tendency of the dissolved substance to remain in the dissolved state. That is to say, the term refers to the ability of the solution to remain homogeneous during a given time interval. Stability can therefore be characterized in a quantifying way by determining said time interval. Thus, the dissolved substance in a first solution characterized by a lower stability exhibits a higher tendency to precipitate or form a colloid, as opposed to a second solution characterized by a higher stability in which said tendency is lower. As a consequence, after a certain amount of time said first solution becomes a heterogeneous mixture whereas said second solution remains a homogeneous mixture.

Turbidity is a measure of water cloudiness caused by the presence of particles in a suspension or a colloid. There are several practical ways of determining turbidity, the most direct being some measure of attenuation (that is, reduction in strength) of light as it passes through a sample column of water. Thus, one way to determine turbidity is visual inspection, i.e., inspection by eye.

Another way of determination is measurement of light attenuation with a photometer. In this regard, the term "Optical density" (also referred to as "OD") denotes a unit-less measure of the transmittance of an optical element for a given length at a given wavelength $\lambda$:

$$OD_{\lambda} = \log_{10} O = -\log_{10}T = -\log_{10}(l/l_0)$$

wherein

O=the per-unit opacity

T=the per-unit transmittance $l_0$=the intensity of the incident light beam l=the intensity of the transmitted light beam.

The higher the optical density, the lower the transmittance. Owing to the scattering of a light beam focused on the particles the optical density of a suspension or a colloid is increased compared to a clear solution.

The composition of a lyophilizate has a consequence for the amount of the solid matter which can be dissolved in a given solvent. However, the composition of a lyophilizate also significantly impacts on the time needed for dissolving the solid matter in the solvent. A central object of the invention was to provide compositions and conditions which accelerate the formation of aqueous solutions of lyophilizates containing a certain amount of proteinaceous constituents. To this end, some further theoretical background is presented aiding the understanding of the invention.

The term "sink conditions" describes a dissolution system that is sufficiently dilute so that the dissolution process is not impeded by approach to saturation of the compound of interest. In the present context, the compound of interest can be each constituent of a particular lyophilizate or the lyophilizate itself.

An important physical measurement required is that of solubility of a compound of interest at a given temperature. Once the solubility is known, the volume of solvent or the acceptability of a particular solvent can be determined. For example, sink conditions are considered to exist if, at the dissolution of 100% of the highest strength of the lyophilizate to be tested, a concentration of preferably not more than about $\frac{2}{3}$, more preferred not more than about $\frac{1}{2}$, even more preferred not more than about $\frac{1}{3}$ of saturation is achieved.

The dissolution of a solid in a bulk liquid is a dynamic process, since molecules migrate from the solid particle into the diffusion layer that surrounds the particle. Then, these molecules diffuse from the diffusion layer into the bulk solution. Provided that during the dissolution of the particles so-called sink conditions are met, the dissolution kinetics are described by Equation (1).

$$C(t)=C_s \times (1-e^{-k \times t}) \qquad (1)$$

With the so-called Noyes-Whitney equation (Noyes, A. A. & Whitney, W. R., J., Am. Chem. Soc. 19 (1897) 930-934), the concentration of the molecule in the bulk solution (c(t)) can be calculated from the concentration of the molecule in the diffusion layer or the so-called solubility of the drug ($c_s$), the time (t) and the rate constant of dissolution ($\xi$). The latter can be calculated by Equation (2) from the surface of the particles (S), the diffusion coefficient of the dissolved molecule ($\xi$), the volume of the bulk solution ($V_s$) and the thickness of the diffusion layer (h).

$$k = \frac{S \times \xi}{Vs \times h} \qquad (2)$$

According to the Stokes Equation (3), the diffusion coefficient ($\xi$) can be calculated from the Boltzmann constant ($k_b$), the temperature (T), the viscosity of the bulk solution (n) and the hydrodynamic radius of the dissolved molecule (r).

$$\xi = \frac{k_b \times T}{6\pi \times \eta \times r} \qquad (3)$$

The surface area (S) of a given volume of a solid lyophilizate is determined by the surface area of the particles. Substitution in Equation (2) shows that for ideal particles the rate constant of dissolution ($\xi$) is inversely proportional to the diameter of the particles.

For several particle sizes one finds that small particles will dissolve much quicker than bigger particles as with smaller particles a larger surface area gets into contact with the solvent. In case the size distribution of the particles gets broader, the average rate constant of dissolution will become less accurate, thus leading to a less accurate prediction of the dissolution profile. That is to say, the dissolution behavior of a lyophilizate is the result of the cumulative effect of all particles in the solid matter.

A first embodiment of the invention is a solid composition obtainable by the steps of (a) preparing a homogeneous solution of an acetate-free preparation of a neutral protease in an aqueous acetate-free low-salt solution; (b) adding a neutral salt to the homogeneous solution of step (a) and dissolving the neutral salt, thereby making a stabilized solution wherein said stabilized solution additionally comprises a buffer salt buffering in the range of about pH 6 to about pH 8.5, and wherein the stabilized solution further comprises calcium chloride; (c) mixing the stabilized solu-tion of step (b) with an acetate-free preparation of one or more proteolytic enzymes with collagenase activity, and making a homogeneous solution; (d) freeze-drying the solu-tion of step (c), thereby obtaining the solid composition of the invention.

The compositions according to the invention are lyophilizates, that is to say products of a freeze-drying process. Said compositions typically have a residual moisture content which is in the range of about 0.01% [w/w] to about 5% [w/w], preferred in the range of 0.1% to 3% [w/w], even more preferred in the range of 1% to 2% [w/w]. Generally, the skilled person aims at minimizing the moisture content since this factor advantageously influences product shelf life.

According to the invention, the lyophilized composition comprising one or more proteolytic enzymes with collage-nase activity and one or more neutral proteases is charac-terized by an enhanced solubility in an aqueous solvent, preferably water, if the composition is free of acetate salt. Examples of an acetate salt are sodium acetate, potassium acetate and calcium acetate.

In Example 2 below a first crystallization process for thermolysin is disclosed. The thermolysin crystals according to this state-of-the-art process form in the presence of calcium acetate, and this acetate salt is comprised in the crystals. In a blending process the acetate crystals can be dissolved but the solution of the neutral protease is instable in that thermolysin tends to precipitate.

The present invention is based on the first finding that the stability of a homogeneous solution of thermolysin is enhanced by the absence of acetate ions. For this reason, an acetate-free preparation of thermolysin has to be provided and used, in order to practice the present invention. To this end, the THERMOASE preparation of thermolysin can be used.

A further important finding of the inventors was that a stable solution of thermolysin is obtained when (i) THER-MOASE is dissolved in a low-salt buffer to yield a homo-geneous solution, and (ii) a neutral salt, preferably sodium chloride, is dissolved subsequently in said homogeneous solution of (i).

In view of the inventor's basic findings, an embodiment of the invention is a solid composition obtainable by the steps of (a) dissolving an acetate-free preparation of a neutral protease, preferably thermolysin from *Bacillus ther-moproteolyticus*, in an aqueous acetate-free low-salt solu-tion, wherein the solution comprises a buffer salt capable of buffering in the range of about pH 6 to about pH 8.5 and further comprises calcium chloride, and making a homoge-neous solution; (b) adding a neutral salt to the homogeneous solution of step (a) and dissolving the neutral salt, thereby making a stabilized solution; (c) mixing the stabilized solu-tion of step (b) with an acetate-free preparation of one or more proteolytic enzymes with collagenase activity, and making a homogeneous solution; (d) freeze-drying the solu-tion of step (c); thereby obtaining the solid composition of the invention.

The low-salt solution of step (a) preferably comprises (and more preferred consists of) water, $CaCl_2$ and an organic buffer salt. The preferred buffer salt is HEPES but other buffer salts are possible. The aggregate concentration of dissolved salts in the low-salt solution of step (a) is prefer-ably in the range of about 1 mM to about 250 mM, more preferred in the range of about 5 mM to about 100 mM, even more preferred in the range of about 10 mM to about 50 mM, and most preferred about 25 mM.

The neutral salt in step (b) is preferably sodium chloride. In a very much preferred embodiment of the invention, prior to step (c) the solution of the neutral protease is subjected to an adjustment of dissolved ions and/or a removal of low molecular weight protein fragments. This can be done, for example, by way of diafiltration. A very much preferred stabilized solution obtained in step (b) preferably comprises thermolysin at a concentration in the range of about 0.5 mg/ml to about 5 mg/ml, more preferred in the range of about 1 mg/ml to about 3 mg/ml. The non-proteinaceous compounds in the solution preferably comprise $CaCl_2$, a neutral salt, and an organic buffer salt capable of buffering in the range of about pH 6 to about pH 8.5. The conductivity of the stabilized solution obtained in step (b) is preferably in the range of about 20 mS/cm to about 23 mS/cm.

A main advantage of the stabilized solution is that the neutral protease, particularly thermolysin, remains stable in homogeneous solution for a longer time, compared to the situation before when state-of-the-art methods involving acetate-containing preparations were used. In blending processes aiming at the formulation of mixtures of several proteases including thermolysin, enhanced stability of the latter protease in solution allows the handling of larger quantities. Thus, more efficient and economic blending processes are possible on the basis if the present invention.

Prior to step (d) the total protein content in the homogeneous solution made in step (c) is preferably in the range of about 1 mg/ml to about 150 mg/ml, more preferred in the range of about 5 mg/ml to about 100 mg/ml. The concentration of $CaCl_2$ in said homogeneous solution made in step (c) is preferably in the range of about 1 mM to about 10 mM, more preferred in the range of about 3 mM to about 5 mM. The concentration of the neutral salt in said homogeneous solution made in step (c) is preferably in the range of about 50 mM to about 500 mM, more preferred in the range of about 50 mM to about 250 mM, even more preferred in the range of about 50 mM to about 200 mM or less than 200 mM.

Figure 1B:
FIG. 1B is a lyophilizate with crystals having a lamellae- or blade-like structure.

As a result of the freeze-drying step (d) of the inventive process a solid composition (lyophilizate) is obtained, wherein the composition is free of acetate salt and wherein the composition comprises one or more proteolytic enzymes with collagenase activity and a neutral protease. Typically, the lyophilizate consists of crystalline matter consisting of lamellae which are aligned in parallel (see also FIG. 1). Apparently, the structure of the lyophilizate provides a very large surface. As a result, upon contacting the lyophilizate with water, the solid matter dissolves very rapidly, usually within 3 min or less.

Rapid formation of a protease solution is an important factor when the protease mixture is to be used in the dissociation of tissue into single cells. The shorter the time to dissolve the proteases, the less proteolytic activity is lost due to auto-proteolysis occurring prior to the application of the proteases to the tissue. Thus, the invention provides an important basis for improved methods of tissue dissociation.

Yet, in more detail, the present invention comprises the following items which are preferred embodiments:

1. A solid composition comprising one or more proteolytic enzymes with collagenase activity (C), and a neutral protease (NP), characterized in that the composition is free of acetate salt.

2. The composition according to item 1, characterized in that the composition comprises sodium chloride, calcium chloride, and a buffer salt, preferably an organic buffer salt.

3. The composition according to any of the items 1 and 2, characterized in that the buffer salt is capable of buffering in the range of about pH 6 to about pH 8.5.

4. The composition according to any of the items 1 to 3, characterized in that the buffer salt is a compound selected from the group consisting of BES (N,N-Bis(2-hydroxyethyl)-2-aminoethanesulfonic acid), Tris (2-Amino-2-(hydroxymethyl)propane-1,3-diol), BisTris (Bis(2-hydroxyethyl)amino-tris(hydroxymethyl)methane), BisTris propane (1,3-bis(tris(hydroxymethyl)methylamino)propane), HEPES (N-(2-hydroxyethyl)-piperazine-N'-2-ethanesulfonic acid), MES (2-(N-morpholino)ethanesulfonic acid), MOPS (3-(N-morpholino)propanesulfonic acid), MOPSO (3-morpholino-2-hydroxypropanesulfonic acid), PIPES (Piperazine-1,4-bis(2-ethanesulfonic acid)), TAPS (N-Tris(hydroxymethyl)methyl-3-aminopropanesulfonic acid), TES (N-Tris(hydroxymethyl)methyl-2-aminoethanesulfonic acid), TEA (Triethanolamine), and Tricine (N-(2-Hydroxy-1,1-bis(hydroxymethyl)ethyl)glycine.

5. The composition according to item 4, characterized in that the buffer salt is HEPES.

6. The composition according to any of the items 1 to 5, characterized in that the composition is a lyophilizate, i.e., obtained by a freeze-drying process.

7. The composition according to any of the items 1 to 6, characterized in that the proteolytic enzymes with collagenase activity in the composition are collagenase I (C1) and/or collagenase II (CII) from *Clostridium histolyticum.*

8. The composition according to any of the items 1 to 7, characterized in that the NP in the composition is thermolysin from *Bacillus thermoproteolyticus.*

9. The composition according to any of the items 1 to 8, characterized in that the weight-by-weight ratio of the neutral protease versus all proteases present in the composition (NP/(NP+C) [w/w]) is in the range of about 1 to about 25.

10. The composition according to item 9, characterized in that NP/(NP+C) [w/w] is in the range of about 2 to about 22.

11. The composition according to item 9, characterized in that NP/(NP+C) [w/w] is about 2.

12. The composition according to item 9, characterized in that NP/(NP+C) [w/w] is about 3.

13. The composition according to item 9, characterized in that NP/(NP+C) [w/w] is about 22.

14. The composition according to any of the items 1 to 13, characterized in that the weight-by-weight ratio of all proteases present in the composition and sodium chloride ((NP+C)/NaCl [w/w]) is in the range of about 0.1 to about 5.

15. The composition according to item 14, characterized in that the (NP+C)/NaCl [w/w] is in the range of about 0.15 to about 3.

16. The composition according to item 14, characterized in that the (NP+C)/NaCl [w/w] is in the range of about 0.18 to about 2.

17. The composition according to item 14, characterized in that the (NP+C)/NaCl [w/w] is about 0.18.

18. The composition according to item 14, characterized in that the (NP+C)/NaCl [w/w] is about 1.3.

19. The composition according to item 14, characterized in that the (NP+C)/NaCl [w/w] is about 2.

20. The composition according to any of the items 1 to 19, characterized in that the weight-by-weight ratio of all proteases present in the composition and calcium chloride hexahydrate ((NP+C)/$CaCl_2$ [w/w]) is in the range of about 10 to about 500.

21. The composition according to item 20, characterized in that (NP+C)/CaCl$_2$ [w/w] is in the range of about 15 to about 470.

22. The composition according to item 20, characterized in that (NP+C)/CaCl$_2$ [w/w] is about 17.5.

23. The composition according to item 20, characterized in that (NP+C)/CaCl$_2$ [w/w] is about 240.

24. The composition according to item 20, characterized in that (NP+C)/CaCl$_2$ [w/w] is about 470.

25. The composition according to any of the items 1 to 24, characterized in that the weight-by-weight ratio of all proteases present in the composition and the buffer salt ((NP+C)/buffer salt [w/w]) is in the range of about 0.05 to about 2.

26. The composition according to item 25, characterized in that (NP+C)/buffer [w/w] is in the range of about 0.1 to about 1.

27. The composition according to item 25, characterized in that (NP+C)/buffer [w/w] is about 0.1.

28. The composition according to item 25, characterized in that (NP+C)/buffer [w/w] is about 0.5.

29. The composition according to item 25, characterized in that (NP+C)/buffer [w/w] is about 1.

30. The composition according to any of the items 25 to 29, characterized in that the buffer salt is selected from the group consisting of BES (N,N-Bis(2-hydroxyethyl)-2-aminoethanesulfonic acid), Tris (2-Amino-2-(hydroxymethyl)propane-1,3-diol), BisTris (Bis(2-hydroxyethyl)amino-tris(hydroxymethyl)methane), BisTris propane (1,3-bis(tris(hydroxymethyl)methylamino)propane), HEPES (N-(2-hydroxyethyl)-piperazine-N' ethanesulfonic acid), MES (2-(N-morpholino)ethanesulfonic acid), MOPS (3-(N-morpholino)propanesulfonic acid), MOPSO (3-morpholino-2-hydroxypropanesulfonic acid), PIPES (Piperazine-1,4-bis(2-ethanesulfonic acid)), TAPS (N-Tris(hydroxymethyl) methyl aminopropanesulfonic acid), TES (N-Tris(hydroxymethyl)methyl-2-aminoethanesulfonic acid), TEA (Triethanolamine), and Tricine (N-(2-Hydroxy-1,1-bis(hydroxymethyl)ethyl)glycine.

31. An aqueous solution comprising water and, in dissolved form, a composition according to any of the items 1 to 30.

32. The aqueous solution according to item 31, characterized in that the pH of the solution is in the range of pH 7 to pH 8, and more preferred pH 7.5.

33. The aqueous solution according to any of the items 31 and 32, characterized in that the concentration of proteases in the solution is in the range of 0.1 mg/ml to 100 mg/ml.

34. The aqueous solution according to item 33, characterized in that the concentration of proteases in the solution is in the range of about 1 mg/ml to about 75 mg/ml.

35. The aqueous solution according to item 34, characterized in that the concentration of proteases in the solution is in the range of about 5 mg/ml to about 50 mg/ml.

36. Use of an aqueous solution according to any of the items 31 to 35 for treating a biological tissue.

37. A kit comprising package material and one or more containers containing a solid composition according to any of the items 1 to 30.

38. The kit according to item 37, characterized in that the one or more containers are sealed, thereby protecting the composition in the containers from moisture.

39. A method to prepare a solution with proteases, comprising the step of contacting a composition according to any of the items 1 to 30 with water.

40. The method according to item 39, characterized in that measured amounts of the composition and water are mixed, in order to yield a concentration of proteases in solution, said concentration being in the range of about 5 mg/ml to about 50 mg/ml.

41. The method according to any of the items 39 and 40, characterized in that a homogeneous solution is obtained within a period in the range of less than about 1 min to 3 min, or within the period of less than 3 min, counted from the moment the composition is contacted with water.

42. The method according to any of the items 40 and 41, characterized in that the concentration of proteases is in the range of about 5 mg/ml to about 30 mg/ml, and a homogeneous solution is obtained within a period of less than about 1 min, counted from the moment the composition is contacted with water.

43. The method according to any of the items 40 and 41, characterized in that the concentration of proteases is in the range of about 15 mg/ml to about 50 mg/ml, and a homogeneous solution is obtained within a period of about 3 min or shorter than 3 min, counted from the moment the composition is contacted with water.

The figures and following examples are provided to aid the understanding of the present invention, the true scope of which is set forth in the appended claims. It is understood that modifications can be made in the procedures set forth without departing from the spirit of the invention.

Example 1: Materials, General Conditions, and Procedures Applied

If not stated otherwise, all aqueous solutions were kept and used at temperatures between 2° C. and 8° C.

*Clostridium histolyticum* collagenases I and II were provided separately, in purified form. Before any of the blending procedures described herein, collagenase I and collagenase II were each purified to homogeneity. Each collagenase was provided in dissolved form, at a concentration of 55 mg/ml in a buffer containing 1 mM CaCl$_2$, 5 mM HEPES, pH 7.5.

The major parts of a freeze drying (lyophilization) procedure include freezing, primary drying (sublimation), and secondary drying (desorption). One objective of freezing is to produce a frozen matrix with sufficient crystal structure to allow the sublimating material to escape. Some products form a glassy material and annealing may be required during the freezing process. Annealing, first lowering the temperature then raising the temperature and then lowering it again, locks the constituents in place and then allows the crystals to grow. Freezing can range from 1 hour to 24 hours, depending on the application. Primary drying (sublimation) drives the unbound moisture out of the product. Sublimation occurs under vacuum with the product temperature below its critical temperature. At the end of the primary drying cycle, the product will usually have 3% to 5% moisture content. Secondary drying (desorption) drives the water which is bound by electrostatic and/or ionic forces from the material. This is done by heating the product. Secondary drying can result in moisture levels of 0.5% or less.

Lyophilizates of protease blends according to the invention were prepared using a lyophilizator containing a chamber with deep-frozen plates and a separate chamber consisting of a condenser all manufactured by HSK (Germany), and according to the instructions by the manufacturer. An exemplary lyophilization process comprised the following steps and conditions:

13

| No. | Step | time (hh:mm) | temp. | pressure | comment |
|-----|------|-------------|-------|----------|---------|
| 1. | loading of enzyme solution | 00:03 | 2° C. | ambient pressure | |
| 2. | Freezing | 00:30 | −50° C. | ambient pressure | temperature may fluctuate by ±4° C. |
| 3. | Freezing | 04:00 | −50° C. | ambient pressure | |
| 4. | Evacuating | 00:20 | −50° C. | 0.01 mbar | |
| 5. | primary drying | 00:40 | −50° C. | 0.01 mbar | |

In the present freeze drying processes, three different regimens for the initial secondary drying were used. One step selected from either 6a, 6b, or 6c was performed.

| No. | Step | time (hh:mm) | temp. | pressure | comment |
|-----|------|-------------|-------|----------|---------|
| 6a. | initial secondary drying | 14:00 | −8° C. | 0.01 mbar | |
| 6b. | initial secondary drying | 20:00 | −8° C. | 0.01 mbar | |
| 6c. | initial secondary drying | 10:00 | 22° C. | 0.01 mbar | temperature may fluctuate by ±3° C. |

Following the initial secondary drying step the following regimen was applied. The partial aeration steps 8. and 10 were optional.

| No. | Step | time (hh:mm) | temp. | pressure | comment |
|-----|------|-------------|-------|----------|---------|
| 7. | secondary drying | 06:00 | 22° C. | 0.01 mbar | |
| 8. | partial aeration (test) | 00:02 | 22° C. | 0.17 mbar | |
| 9. | secondary drying | 03:30 | 22° C. | 0.01 mbar | |
| 10. | partial aeration (test) | 00:02 | 22° C. | 0.05 mbar | |
| 11. | aeration with $N_2$ | 00:01 | 22° C. | 700 mbar | |
| 12. | incubation | 00:05 | 22° C. | 700 mbar | |
| 13. | aeration with $N_2$ | 00:01 | 22° C. | ambient pressure | |
| 14. | unloading | 00:03 | 4° C. | ambient pressure | |
| 15. | storage | | 4° C. | ambient pressure | |

Example 2: Preparation of Crystallized Thermolysin and Solubilization of Crystallized Thermolysin Thermolysin (EC 3.4.24.27) was obtained as a freeze-dried, amorphous powder from Daiwa Kasei K. K. (Japan) containing at least about 60% [w/w] of enzyme protein, about 20% [w/w] of anhydrous Calcium acetate (Ca-acetate or CaAc), and about 10% [w/w] of anhydrous Sodium acetate (Na-acetate or NaAc). In case thermolysin in the presence of acetate was used, twice crystallized thermolysin was used. For a crystallization step, thermolysin lyophilizate was suspended at a concentration in the range of between about 1% [w/v] to about 3% [w/v] in an ice-cold aqueous solution of Calcium acetate at a concentration of 0.01 M. thermolysin was dissolved by adding 0.2 N NaOH drop-wise and under agitation, until the pH of the solution was between pH 11.0 and pH 11.4. After removal of any undissolved residue (if found to be present), the solution was neutralized to pH 6.0 with 0.2 N acetic acid. Crystallization usually was complete after about 2 days. During the whole process ice-cold temperatures were maintained. The crystals were recovered and freeze-dried under standard conditions.

An exemplary lyophilizate of crystallized thermolysin had a protein content of about 66.1% [w/w] and was used in blending experiments.

Before blending, the crystallized thermolysin lyophilizate was suspended in aqueous HEPES buffer (1 mM $CaCl_2$, 5 mM HEPES, pH 7.5). In order to dissolve the protein, about 7.2 mM NaOH were added (as 0.1 N NaOH) to raise the pH to a value of about pH 11. Subsequently, the pH was lowered to pH 7.5 by admixing 0.5 M HEPES solution which was not titrated with hydroxide and therefore acidic. The final volume of the solution was adjusted with HEPES buffer (1 mM $CaCl_2$, 5 mM HEPES, pH 7.5). The final protein concentration in the solution was between 13.1 mg/ml and 13.2 mg/ml. Notably, a clear solution was obtained which, however, was not stable. It was observed that the resulting solution became turbid after about 30 min due to beginning precipitation of thermolysin. Only small amounts of thermolysin solution could be prepared using the above method. As a further disadvantage, the small volume of thermolysin solution had to be used instantly in the blending process in which enzyme in homogeneous solution is required. Because the blending process takes a certain amount of time it has to be assured that the thermolysin enzyme solution is homogeneous during the whole process.

Example 3: Preparation of a Stabilized Solution Containing Thermolysin

In view of the shortcomings described in Example 2, a more favorable method for providing thermolysin in homogeneous solution was developed. A further preparation containing crude thermolysin (EC 3.4.24.27) is available from Daiwa Kasei K. K. (Japan) under the trade name THER-MOASE. The THERMOASE quality of thermolysin used here was a lyophilisate. The protein content of "crude thermolysin" in the lyophilizate was about 33% [w/w]. About 65% [w/w] of the lyophilisate was NaCl. The remaining amount of about 2% [w/w] was $Na_2SO_4$. "Crude thermolysin" in the present context is a protein mixture consisting of (i) about 70% substantially undegraded (intact) thermolysin, (ii) about 24% of thermolysin degradation products which retain proteolytic activity (to different degrees), and (iii) about 6% of proteolytically inactive fragments and further impurities.

A volume of 6.5 I of an aqueous buffer containing 5 mM $CaCl_2$, 20 mM HEPES, pH 7.5 was prepared. An amount of 200 g dry THERMOASE lyophilisate was dissolved in the aqueous buffer and a clear solution was obtained. Subsequently, 935 g solid NaCl was added and dissolved in the solution. The volume of the solution was adjusted to 8 I by adding a further volume of the aqueous buffer containing 5 mM $CaCl_2$, 20 mM HEPES, pH 7.5, and mixing by stirring. A homogeneous solution was obtained. Taking into account that about 65% [w/w] of the lyophilisate consists of NaCl, the final NaCl concentration in the solution was about 2.3 M. The final concentration of crude thermolysin (about 33% [w/w] of the lyophilisate) in the solution was about 8.25 mg/ml corresponding to a concentration of substantially undegraded thermolysin of about 5.8 mg/ml in the solution.

The solution of thermolysin produced as described above was stable for at least 20 hours and up to 48 hours. That is to say, no precipitate was formed in the solution during this time. Under other conditions, particularly when the amount of NaCl was dissolved in the buffer prior to adding THER-MOASE lyophilizate, beginning precipitation of thermolysin could be observed after about an hour. Therefore the stabilized solution containing thermolysin allowed extensive further processing, including removal of small proteolytic fragments by way of diafiltration, and subsequent blending using larger volumes of thermolysin solution.

Diafiltration was performed using a filter with an exclusion limit of about 10 kDa and against an aqueous buffer containing 5 mM $CaCl_2$, 170 mM NaCl, 20 mM HEPES, pH 7.5. The final protein concentration after diafiltration was between about 2.25 mg/ml and about 2.75 mg/ml in the diafiltration buffer. The conductivity of the diafiltrated thermolysin solution was $21.2 \pm 1$ mS/cm.

Diafiltrated thermolysin was either used directly in blending processes, or the solution was aliquoted and aliquots were frozen and stored at $-20°$ C. Frozen aliquots were thawed before use and remained stable afterwards for 6 hours or more.

Example 4: Preparation of a Lyophilized Thermolysin-Containing Blend of Proteases (Blend 1) with a Low Amount of Thermolysin The blend contained collagenase I, collagenase II and thermolysin. Collagenase solutions according to Example 1 and thermolysin solution according to Example 2 were mixed according to Table 1. The resulting mixture had the final volume as indicated in the table and was lyophilized immediately after addition of the last component. The lyophilizate which was obtained consisted of white crystals which in the freeze-drying process formed unordered clusters. The morphology of the lyophilizate corresponded to the lyophilizate depicted in FIG. 1A.

TABLE 1

| substance | amount (absolute) | concentration in stock solution | vol. of stock solution in mixture | concentration in final mixture |
|---|---|---|---|---|
| collagenase I | 26,565 mg | 55 mg/ml | 483 ml | 29.3 mg/ml |
| collagenase II | 17,435 mg | 55 mg/ml | 317 ml | 19.2 mg/ml |
| thermolysin | 1,265 mg $ | 13.2 mg/ml | 96.6 ml | 1.4 mg/ml |
| Protein conc. total | 45,265 mg | | | 49.9 mg/ml |
| NaAc total | | | | 2.6 mM |
| CaAc total | | | | 3 mM |
| $CaCl_2$ total | | | | 0.8 mM |
| NaOH | | 0.1N | 9 ml | 1 mM |
| HEPES total | | | | 5.2 mM |
| HEPES‡ | | 0.5M | 1.5 ml | |
| HEPES§ | | buffer | — | |
| Volume total | 907.1 ml | | | |
| pH | 7.5 | | | |

‡HEPES solution, not alkali-titrated; for neutralization
§HEPES buffer (1 mM $CaCl_2$, 5 mM HEPES, pH 7.5) for volume adjustment, if necessary
$ corresponding to 1,914 mg of lyophilized crystals (i.e., including solid Calcium acetate, see Example 2)

Example 5: Preparation of a Lyophilized Thermolysin-Containing Blend of Proteases (Blend 2) with a Medium Amount of Thermolysin The blend contained collagenase I, collagenase II and thermolysin. Collagenase solutions according to Example 1 and thermolysin solution according to Example 2 were mixed according to Table 2. The resulting mixture had the final volume as indicated in the table and was lyophilized immediately after addition of the last component. The lyophilizate which was obtained consisted of white crystals which in the freeze-drying process formed unordered clusters. The morphology of the lyophilizate corresponded to the lyophilizate depicted in FIG. 1A.

TABLE 2

| substance | amount (absolute) | concentration in stock solution | volume of stock solution in mixture | concentration in final mixture |
|---|---|---|---|---|
| collagenase I | 8,580 mg | 55 mg/ml | 156 ml | 8.2 mg/ml |
| collagenase II | 5,610 mg | 55 mg/ml | 102 ml | 5.4 mg/ml |
| thermolysin | 5,585 mg $ | 13.1 mg/ml | 422 ml | 5.3 mg/ml |
| Protein total | 19,775 mg | | | 18.9 mg/ml |
| NaAc total | | | | 9.9 mM |
| CaAc total | | | | 11.6 mM |

TABLE 2-continued

| substance | amount (absolute) | concentration in stock solution | volume of stock solution in mixture | concentration in final mixture |
|---|---|---|---|---|
| CaCl₂ total | | | | 0.5 mM |
| NaOH | | 0.1N | 75 ml | 7.2 mM |
| HEPES total | | | | 5.9 mM |
| HEPES‡ | | 0.5M | 7 ml | |
| HEPES§ | | buffer solution | 283 ml | |
| Volume total | 1,045 ml | | | |
| pH | 7.5 | | | |

‡HEPES solution, not alkali-titrated; for neutralization
§HEPES buffer (1 mM CaCl₂, 5 mM HEPES, pH 7.5) for volume adjustment, if necessary
$ corresponding to 8,449 mg of lyophilized crystals (i.e., including solid Calcium acetate, see Example 2)

Example 6: Preparation of a Lyophilized Thermolysin-Containing Blend of Proteases (Blend 3) with a High Amount of Thermolysin The blend contained collagenase I, collagenase II and thermolysin. Collagenase solutions according to Example 1 and thermolysin solution according to Example 2 were mixed according to Table 3. The resulting mixture had the final volume as indicated in the table and was lyophilized immediately after addition of the last component. The lyophilizate which was obtained consisted of white crystals which in the freeze-drying process formed unordered clusters. The morphology of the lyophilizate corresponded to the lyophilizate depicted in FIG. 1A.

TABLE 3

| substance | amount (absolute) | concentration in stock solution | volume of stock solution in mixture | concentration in final mixture |
|---|---|---|---|---|
| collagenase I | 2,140 mg | 55 mg/ml | 38.9 ml | 5.6 mg/ml |
| collagenase II | 1,422 mg | 55 mg/ml | 25.85 ml | 3.7 mg/ml |
| thermolysin | 2,772 mg $ | 13.2 mg/ml | 211 ml | 7.2 mg/ml |
| Protein total | 6,334 mg | | | 16.5 mg/ml |
| NaAc total | | | | 13.4 mM |
| CaAc total | | | | 15.7 mM |
| CaCl2 total | | | | 0.4 mM |
| NaOH | | 0.1N | 19 ml | 5 mM |
| HEPES total | | | | 4.5 mM |
| HEPES‡ | | 0.5M | 2 ml | |
| HEPES§ | | buffer solution | 85.75 ml | |
| Volume total | 382.5 ml | | | |
| pH | 7.5 | | | |

‡HEPES solution, not alkali-titrated; for neutralization
§HEPES buffer (1 mM CaCl₂, 5 mM HEPES, pH 7.5) for volume adjustment, if necessary
$ corresponding to 4,194 mg of lyophilized crystals (i.e., including solid Calcium acetate, see Example 2)

Example 7: Preparation of an Acetate-Free Thermolysin-Containing Blend of Proteases (Blend 4)

The blend contained collagenase I, collagenase II and thermolysin. Collagenase solutions according to Example 1 and diafiltrated stabilized thermolysin solution according to Example 3 were mixed according to Table 4. The resulting mixture had the final volume as indicated in the table and was lyophilized immediately after addition of the last component. The lyophilizate which was obtained consisted of white crystals which in the freeze-drying process formed lamellae or blade-like structures of which most were aligned in parallel. The morphology of the lyophilizate corresponded to the lyophilizate depicted in FIG. 1B.

TABLE 4

| substance | amount (absolute) | | concentration in stock solution | volume of stock solution in mixture | concentration in final mixture | |
|---|---|---|---|---|---|---|
| collagenase I | 410 | mg | 55 mg/ml | 7.45 ml | 16 | mg/ml |
| collagenase II | 275 | mg | 55 mg/ml | 5 ml | 10.7 | mg/ml |
| thermolysin‡ | 33 | mg | 2.5 mg/ml | 13.2 ml | 1.3 | mg/ml |
| Protein total | 718 | mg | | | 28 | mg/ml |
| CaCl₂ total | | | | | 3.1 | mM |
| NaCl | | | | | 87 | mM |
| HEPES total | | | | | 12.8 | mM |
| Volume total | 25.65 | ml | | | | |
| pH | 7.5 | | | | | |

‡the total amount of protein present in the stabilized solution after diafiltration, see Example 3

Example 8: Preparation of an Acetate-Free Thermolysin-Containing Blend of Proteases (Blend 5)

The blend contained collagenase I, collagenase II and thermolysin. Collagenase solutions according to Example 1 and diafiltrated stabilized thermolysin solution according to Example 3 were mixed according to Table 5. The resulting mixture had the final volume as indicated in the table and was lyophilized immediately after addition of the last component. The lyophilizate which was obtained consisted of white crystals which in the freeze-drying process formed lamellae or blade-like structures of which most were aligned in parallel. The morphology of the lyophilizate corresponded to the lyophilizate depicted in FIG. 1B.

TABLE 5

| substance | amount (absolute) | | concentration in stock solution | volume of stock solution in mixture | concentration in final mixture | |
|---|---|---|---|---|---|---|
| collagenase I | 660 | mg | 55 mg/ml | 12 ml | 2.85 | mg/ml |
| collagenase II | 440 | mg | 55 mg/ml | 8 ml | 1.9 | mg/ml |
| thermolysin‡ | 530 | mg | 2.5 mg/ml | 212 ml | 2.3 | mg/ml |
| Protein total | 1,630 | mg | | | 7.05 | mg/ml |
| CaCl₂ total | | | | | 4.7 | mM |
| NaCl | | | | | 155 | mM |
| HEPES total | | | | | 18.7 | mM |
| Volume total | 232 | ml | | | | |
| pH | 7.5 | | | | | |

‡the total amount of protein present in the stabilized solution after diafiltration, see Example 3

Example 9: Preparation of an Acetate-Free Thermolysin-Containing Blend of Proteases (Blend 6)

The blend contained collagenase I, collagenase II and thermolysin. Collagenase solutions according to Example 1 and diafiltrated stabilized thermolysin solution according to Example 3 were mixed according to Table 6. The resulting mixture had the final volume as indicated in the table and was lyophilized immediately after addition of the last component. The lyophilizate which was obtained consisted of white crystals which in the freeze-drying process formed lamellae or blade-like structures of which most were aligned in parallel. The morphology of the lyophilizate corresponded to the lyophilizate depicted in FIG. 1B.

TABLE 6

| substance | amount (absolute) | concentration in stock solution | volume of stock solution in mixture | concentration in final mixture |
|---|---|---|---|---|
| collagenase I | 660 mg | 55 mg/ml | 12 ml | 1.5 mg/ml |
| collagenase II | 440 mg | 55 mg/ml | 8 ml | 1 mg/ml |
| thermolysin‡ | 1,060 mg | 2.5 mg/ml | 424 ml | 2.4 mg/ml |
| Protein total | 2,160 mg | | | 4.9 mg/ml |
| CaCl₂ total | | | | 4.8 mM |
| NaCl | | | | 162 mM |
| HEPES total | | | | 19.3 mM |
| Volume total | 444 ml | | | |
| pH | 7.5 | | | |

‡the total amount of protein present in the stabilized solution after diafiltration, see Example 3

Example 10: Solubilization of Lyophilizates

Lyophilized blends in sealed bottles were dissolved in different amounts of purified water, in order to yield solutions with different protein concentrations. The bottles were put on a roller device and agitated at 32 revolutions per minute at 20° C. The time needed to dissolve the lyophilizates was recorded. Recordings were stopped after 75 min, even if solubilization was not complete at this point. Table 7 indicates the time intervals needed for dissolving the lyophilizates according to each of Example 4 to 9. Completeness of solubilization (i.e., the fact whether or not a homogeneous solution was obtained) was assessed by visual inspection or by turbidity measurements.

TABLE 7

| Blend # | protein concentration in solution (after solubilization), in [mg/ml] | time needed for solubilization, in [min] |
|---|---|---|
| 1 | 49.9 | 3 |
| 1 | 25 | 3 |
| 2 | 18.9 | 75 |
| 2 | 7 | 75 |
| 3 | 16.5 | 75 |
| 3 | 5.5 | 75 |
| 4 | 47 | 3 |
| 4 | 28 | <1 |
| 5 | 21 | 3 |
| 5 | 7 | <1 |
| 6 | 17 | 3 |
| 6 | 5 | <1 |

Example 11: Solubilization of Lyophilizates

Under the same conditions as described in Example 10, lyophilized blends in sealed bottles were dissolved in different amounts of purified water, in order to yield solutions with different protein concentrations. The time needed to dissolve the lyophilizates was recorded. Recordings were stopped after 75 min, even if solubilization was not complete at this point. Completeness of solubilization was firstly assessed by visual inspection. Secondly. the turbidity of each obtained solution was measured by determining its optical density (OD) at a wavelength 600 nm using standard quartz cuvettes and a photometer. Table 8 indicates the time intervals needed for dissolving the lyophilizates as well as the results of the assessments of turbidity.

TABLE 8

| Blend # | protein concentration in solution (after solubilization), in [mg/ml] | time needed for solubilization, in [min] | turbidity as determined by OD at 600 nm | turbidity as determined by visual inspection |
|---|---|---|---|---|
| 1 | 49.9 | 3 | 0.013 | clear |
| 1 | 25 | 3 | 0.014 | clear |
| 2 | 18.9 | 75 | 2.159¥ | opaque, precipitate |
| 2 | 7 | 75 | 0.979 | opaque, precipitate |
| 3 | 16.5 | 75 | 2.127¥ | opaque, precipitate |
| 3 | 5.5 | 75 | 1.665 | opaque, precipitate |
| 4 | 47 | 3 | 0.033 | clear |
| 4 | 28 | <1 | 0.026 | clear |
| 5 | 21 | 3 | 0.078 | clear |
| 5 | 7 | <1 | 0.037 | clear |
| 6 | 17 | 3 | 0.088 | clear |
| 6 | 5 | <1 | 0.078 | clear |

¥measurement out of range of proportionality

The invention claimed is:

1. A solid composition obtained or obtainable by the steps of (a) preparing a first homogeneous solution of an acetate-free preparation of a neutral protease (NP) in an aqueous acetate-free low-salt solution, the aggregate concentration of salt(s) in said low-salt solution being in the range of about 1 mM to about 250 mM;

(b) adding a neutral salt to the first homogeneous solution of step (a) and dissolving the neutral salt, thereby making a stabilized solution, wherein said stabilized solution additionally comprises a buffer salt buffering in the range of about pH 6 to about pH 8.5, and wherein the stabilized solution further comprises calcium chloride;

(c) mixing the stabilized solution of step (b) with an acetate-free preparation of one or more proteolytic enzymes with collagenase activity (C), and making a second homogeneous solution; and (d) freeze-drying the solution of step (c), thereby obtaining the solid composition, wherein:

the neutral protease is thermolysin;

the neutral salt is sodium chloride; and a total protein content in the second homogeneous solution is in the range of 1 mg/ml to 150 mg/ml, a concentration of the calcium chloride is in the range of 1 mM to about 10 mM, and a concentration of sodium chloride in the second homogeneous solution is in the range of about 50 mM to about 500 mM.

2. The solid composition of claim 1, wherein the neutral protease is thermolysin from *Bacillus thermoproteolyticus*.

3. The solid composition of claim 1, wherein the acetate-free low-salt solution in step (a) comprises a buffer salt buffering in the range of about pH 6 to about pH 8.5.

4. The solid composition of claim 1, wherein the acetate-free low-salt solution in step (a) further comprises calcium chloride.

5. The solid composition of claim 1, wherein the stabilized solution in step (b) comprises the neutral protease at a concentration in the range of about 0.5 mg/ml to about 5 mg/ml.

6. The solid composition of claim 1, wherein in step (b) the conductivity of the stabilized solution is in the range of about 20 mS/cm to about 23 mS/cm.

7. The solid composition of claim 1, wherein in step (b) the buffer salt is a compound selected from the group consisting of BES (N,NBis(2-hydroxyethyl)-2-aminoethanesulfonic acid), Tris (2-Amino-2-hydroxymethyl)propane-1,3-diol), BisTris (Bis(2-hydroxyethyl)amino-tris(hydroxymethyl)methane), BisTris propane (1,3-bis(tris (hydroxymethyl)methylamino)propane), HEPES (N-(2-hydroxyethyl)-piperazine-N'-2-ethanesulfonic acid), MES (2-(Nmorpholino) ethanesulfonic acid), MOPS (3-(Nmorpholino) propanesulfonic acid), MOPSO (3-morpholino-2-hydroxypropanesulfonic acid), PIPES (Piperazine-1,4-bis (2-ethanesulfonic acid)), TAPS (N-Tris(hydroxymethyl) methyl-3-aminopropanesulfonic acid), TES (N-Tris(hydroxymethyl) methyl-2-aminoethanesulfonic acid), TEA (Trietha-nolamine), and Tricine (N-(2-Hydroxy-1,1-bis (hydroxymethyl)ethyl)glycine.

8. The solid composition of claim 1, wherein said method further comprises removing small proteolytic fragments from the solution produced by step (b) via diafiltration before performing step (c).

9. The solid composition of claim 1, wherein the composition comprises sodium chloride, calcium chloride, and an organic buffer salt.

10. The solid composition of claim 1, wherein the solid composition is crystalline matter consisting of lamellae which are aligned in parallel.

11. The solid composition of claim 1, wherein the weight-by-weight ratio of all proteases present in the composition and sodium chloride (=(NP+C)/NaCl [w/w]) is in the range of about 0.1 to about 5.

12. The solid composition of claim 1, wherein the weight-by-weight ratio of all proteases present in the composition and calcium chloride hexahydrate (=(NP+C)/CaCl$_2$ [w/w]) is in the range of about 10 to about 500.

13. The solid composition of claim 1, wherein the weight-by-weight ratio of all proteases present in the composition and the buffer salt (=(NP+C)/buffer [w/w]) is in the range of about 0.05 to about 2.

14. The solid composition of claim 1, wherein step (a) comprises preparing a homogeneous solution of an acetate-free preparation of thermolysin in an aqueous acetate-free low-salt solution, wherein the acetate-free low-salt solution comprises a buffer salt buffering in the range of about pH 6 to about pH 8.5, wherein the acetate-free low-salt solution further comprises calcium chloride, and wherein the aggregate concentration of salt(s) in the acetate-free low-salt solution is in the range of about 1 mM to about 250 mM.

15. The solid composition of claim 1, wherein step (b) comprises adding sodium chloride to the homogeneous solution of step (a) and dissolving the sodium chloride, thereby making a solution, wherein the solution comprises the buffer salt buffering in the range of about pH 6 to about pH 8.5, and wherein the solution comprises the thermolysin at a concentration in the range of about 0.5 mg/ml to about 5 mg/ml, and calcium chloride, and the conductivity of the solution is in the range of about 20 mS/cm to about 23 mS/cm, wherein the buffer salt is a compound selected from the group consisting of BES (N,NBis(2-hydroxyethyl)-2-aminoethanesulfonic acid), Tris (2-Amino-2-hydroxymethyl)propane-1,3-diol), BisTris (Bis(2-hydroxyethyl) amino-tris(hy-droxymethyl)methane), BisTris propane (1,3-bis(tris (hydroxymethyl)methylamino)propane), HEPES (N-(2-hydroxyethyl)-piperazine-N'-2-ethanesulfonic acid), MES (2-(Nmorpholino) ethanesulfonic acid), MOPS (3-(Nmorpholino)propanesulfonic acid), MOPSO (3-morpholino-2-hydroxypropanesulfonic acid), PIPES (Piperazine-1,4-bis(2-ethanesulfonic acid)), TAPS (N-Tris (hydroxymethyl)methyl-3-aminopropanesulfonic acid), TES (N-Tris(hydroxymethyl) methyl-2-aminoethanesulfonic acid), TEA (Trietha-nolamine), and Tricine (N-(2-Hydroxy-1,1-bis(hydroxymethyl)ethyl)glycine.

16. The solid composition of claim 1, wherein said method comprises the steps of
   (a) preparing a homogeneous solution of an acetate-free preparation of thermolysin in an aqueous acetate-free low-salt solution, wherein the acetate-free low-salt solution comprises a buffer salt buffering in the range of about pH 6 to about pH 8.5, wherein the acetate-free low-salt solution further comprises calcium chloride, and wherein the aggregate concentration of salt(s) in the acetate-free low-salt solution is in the range of about 1 mM to about 250 mM;
   (b) adding sodium chloride to the homogeneous solution of step (a) and dissolving the sodium chloride, thereby making a solution, wherein the solution comprises the buffer salt buffering in the range of about pH 6 to about pH 8.5, and wherein the solution comprises the thermolysin at a concentration in the range of about 0.5 mg/ml to about 5 mg/ml, and calcium chloride, and the conductivity of the solution is in the range of about 20 mS/cm to about 23 mS/cm, wherein the buffer salt is a compound selected from the group consisting of BES (N,NBis(2-hydroxyethyl)-2-aminoethanesulfonic acid), Tris (2-Amino-2-hydroxymethyl)propane-1,3-diol), BisTris (Bis(2-hydroxyethyl)amino-tris(hy-droxymethyl)methane), BisTris propane (1,3-bis(tris (hydroxymethyl)methylamino)propane), HEPES (N-(2-hydroxyethyl)-piperazine-N'-2-ethanesulfonic acid), MES (2-(Nmorpholino) ethanesulfonic acid), MOPS (3-(Nmorpholino)propanesulfonic acid), MOPSO (3-morpholino-2-hydroxypropanesulfonic acid), PIPES (Piperazine-1,4-bis(2-ethanesulfonic acid)), TAPS (N-Tris(hydroxymethyl)methyl-3-aminopropanesulfonic acid), TES (N-Tris(hydroxymethyl) methyl-2-aminoethanesulfonic acid), TEA (Trietha-nolamine), and Tricine (N-(2-Hydroxy-1,1-bis (hydroxymethyl)ethyl)glycine;
   (b1) removing small proteolytic fragments from the solution produced by step (b) via diafiltration;
   (c) mixing the solution of step (b1) with an acetate-free preparation of one or more proteolytic enzymes with collagenase activity, and making a homogeneous solution, wherein the total protein content in the homogeneous solution is in the range of 1 mg/ml to 150 mg/ml, the concentration of calcium chloride is in the range of 1 mM to about 10 mM, and the concentration of sodium chloride is in the range of 50 mM to 500 mM; and (d) freeze-drying the solution of step (c), thereby obtaining the solid composition, wherein the solid composition is crystalline matter consisting of lamellae which are aligned in parallel.

* * * * *